(12) United States Patent
Tetzner et al.

(10) Patent No.: US 9,863,001 B2
(45) Date of Patent: Jan. 9, 2018

(54) METHOD FOR THE DETECTION OF CYTOSINE METHYLATIONS IN DNA

(75) Inventors: Reimo Tetzner, Berlin (DE); Jürgen Distler, Berlin (DE)

(73) Assignee: EPIGENOMICS AG, Berlin (DE)

( * ) Notice: Subject to any disclaimer, the term of this patent is extended or adjusted under 35 U.S.C. 154(b) by 1133 days.

(21) Appl. No.: 10/568,300

(22) PCT Filed: Aug. 13, 2004

(86) PCT No.: PCT/DE2004/001837
§ 371 (c)(1),
(2), (4) Date: Feb. 15, 2006

(87) PCT Pub. No.: WO2005/024056
PCT Pub. Date: Mar. 17, 2005

(65) Prior Publication Data
US 2006/0194208 A1    Aug. 31, 2006

(30) Foreign Application Priority Data
Aug. 15, 2003   (DE) .................................. 103 38 308

(51) Int. Cl.
*C12Q 1/68*   (2006.01)
(52) U.S. Cl.
CPC ..... *C12Q 1/6886* (2013.01); *C12Q 2600/106* (2013.01); *C12Q 2600/154* (2013.01)
(58) Field of Classification Search
CPC ............ C12Q 1/6818; C12Q 2525/301; C12Q 1/6827; C12Q 2565/1015; C12Q 2600/154
See application file for complete search history.

(56) References Cited

U.S. PATENT DOCUMENTS

| | | | |
|---|---|---|---|
| 5,525,494 A | 6/1996 | Newton | |
| 5,786,146 A | 7/1998 | Herman et al. | |
| 6,017,704 A | 1/2000 | Herman et al. | |
| 6,090,552 A * | 7/2000 | Nazarenko | C12Q 1/6818 435/6.12 |
| 6,200,756 B1 | 3/2001 | Herman et al. | |
| 6,326,145 B1 | 12/2001 | Whitcombe et al. | |
| 6,331,393 B1 | 12/2001 | Laird et al. | |
| 6,365,729 B1 | 4/2002 | Tyagi et al. | |
| 2003/0017465 A1 * | 1/2003 | Kay ................................. | 435/6 |
| 2003/0082600 A1 | 5/2003 | Olek et al. | |
| 2003/0087240 A1 * | 5/2003 | Whitcombe | C12Q 1/6818 435/6.11 |
| 2004/0115663 A1 | 6/2004 | Berlin et al. | |
| 2004/0152080 A1 | 8/2004 | Berlin | |
| 2004/0265814 A1 * | 12/2004 | Distler et al. ..................... | 435/6 |
| 2005/0118613 A1 * | 6/2005 | Iacopetta ......................... | 435/6 |
| 2005/0287553 A1 | 12/2005 | Guetig et al. | |
| 2006/0057561 A1 * | 3/2006 | Hart ................................. | 435/5 |
| 2006/0183128 A1 * | 8/2006 | Berlin et al. ..................... | 435/6 |
| 2007/0264653 A1 * | 11/2007 | Berlin et al. ..................... | 435/6 |
| 2008/0220418 A1 | 9/2008 | Ballhause et al. | |

FOREIGN PATENT DOCUMENTS

| | | |
|---|---|---|
| DE | 199 51 189 A1 | 5/2001 |
| DE | 10019173 A1 | 10/2001 |
| DE | 10029915 A1 | 1/2002 |
| DE | 10154317 A1 | 5/2003 |
| EP | 0 416 817 A2 | 3/1991 |
| WO | WO 99/66071 A1 | 12/1999 |
| WO | 00/70090 A1 | 11/2000 |
| WO | 0192565 A2 | 12/2001 |
| WO | 02/072880 A2 | 9/2002 |

OTHER PUBLICATIONS

Eads et a. Nucleic acids research 2000 VOl. 28 p. e32.*
Solinas et al. Nucleic Acids Research 2001 VOl. 29 p. e96.*
Grunau et al. Nucleic Acids Research 2001 VOl. 29 p. e65.*
Broude et al. (Trends in Biotechnology 2002 VOl 20 p. 249).*
Whitcombe et al. (Nature Biotechnoogy 1999 vol. 17 p. 804).*
Thelwell et al., "Mode of action and application of Scorpion primers to mutation detection," Nucleic Acids Research, 28(19):3752-61 (2000).
Enrich et al., "A new method for accurate assessment of DNA quality after bisulfite treatment," Nucleic Acids Research, 35(5):e29 (pp. 1-8) (2007).
Dahl et al. (2003) "DNA methylation analysis techniques," Biogerontol. 4:233-250.
Frommer et al. (1992) "A genomic sequencing protocol that yields a positive display of 5-methylcytosine residues in individual DNA strands," Proc. Natl. Acad. Sci. USA. 89(5): 1827-1831.
Genbank Database [online] (Jul. 26, 2016) "*Homo sapiens* BRCA1 (BRCA1) gene, complete cds; ribosomal protein L21-like protein (rpL21) pseudogene, complete sequence; Rho? (Rho7) and Vatl (Vatl) genes, complete cds; and unknown (ifp35) gene, exons 1 through 3 and partial cds," Accession No. L78833. National Center for Biotechnology Information. Accessible on the Internet at URL: https://www.ncbi.nlm.nih.gov/nuccore/L78833.1. [Last Accessed Mar. 10, 2017].

(Continued)

*Primary Examiner* — Katherine Salmon
(74) *Attorney, Agent, or Firm* — Lathrop Gage LLP; James H. Velema, Esq.

(57) ABSTRACT

The invention relates to a method for analyzing cytosine methylations in DNA sequences, according to which non-methylated cytosines are first converted into uracil while 5-methylcytosine remains unmodified. The DNA is then amplified by means of a polymerase and at least one primer whose 5 end is connected to a probe via a linker. The probe is intramolecularly hybridized onto the amplified products in accordance with the methylation state of the DNA, hybridization being detectable via different detection systems. The inventive method is particularly suitable for diagnosing and predicting cancer diseases and other diseases associated with a modification of the methylation state as well as for predicting undesired effects of medicaments.

16 Claims, 6 Drawing Sheets

(56) References Cited

OTHER PUBLICATIONS

Genbank Database [online] (Jun. 24, 2003) "*Homo sapiens* glutathione S-transferase pi (GSTP1) gene, complete cds," Accession No. AY324387. National Center for Biotechnology Information. Accessible on the Internet at URL: https://www.ncbi.nlm.nih.gov/nuccore/AY324387. [Last Accessed Mar. 10, 2017].

Herman et al. (1996) "Methylation-specific PCR: a novel PCR assay for methylation status of CpG islands," Proc. Natl. Acad. Sci. USA. 93(18):9821-9826.

Millar et al. (2003) "Five not four: History and significance of the fifth base," In: The Epigenome. Eds. Beck et al. Wiley-VCH Publishers. Weinheim, Germany. pp. 3-20.

Olek et al. (1996) "A modified and improved method for bisulphite based cytosine methylation analysis," Nucleic Acids Res. 24(24): 5064-5066.

Palmisano et al. (2000) "Predicting lung cancer by detecting aberrant promoter methylation in sputum," Cancer Res. 60(21):5954-5958.

Saha et al. (2001) "Quantitation of HIV-1 by real-time PCR with a unique fluorogenic probe," Virological Methods. 93:33-42.

International Search Report with Written Opinion corresponding to International Patent Application No. PCT/DE2004/001837, dated Mar. 21, 2005.

Lo et al., Cancer Research, 59:3899-903 (1999).
Eads et al., Nucleic Acids Research, 28(8):e32(i-viii) (2000).
Solinas et al., Nucleic Acids Research, 29(20):e96(1-9) (2001).
Pinero et al., American Biotechnology Laboratory, 21(4):40-1 (2003).
McKeen et al., Organic & Biomolecular Chemistry, 1(13):2267-75 (2003).
Whitcombe et al., Nature Biotechnology, 17(8):804-7 (1999).
Thelwell et al., Nucleic Acids Research, 28(19):3752-61 (2000).
Walker, Journal of Biochemical and Molecular Toxicology, 15(3):121-7 (2001).
Cottrell et al., Ann. N. Y. Acad. Sci., 983:120-30 (2003).
Liu et al., Analytical Biochemistry, 317(2):259-65 (2003).
Laird et al., Nature Reviews Cancer, 3(4):253-66 (2003).
Rand et al., Methods, 27:114-20 (2002).
Trinh et al., Methods, 25:456-62 (2001).
Bransteitter et al., PNAS, 100(7):4102-7 (2003).
Pham et al., Nature, 424(6944):103-7 (2003).

\* cited by examiner

METHOD FOR THE DETECTION OF CYTOSINE METHYLATIONS IN DNA

BACKGROUND OF THE INVENTION

The present invention concerns a method for the detection of 5-methylcytosine in DNA. 5-Methylcytosine is the most frequent covalently modified base in the DNA of eukaryotic cells. It plays an important biological role, among other things, in the regulation of transcription, in genetic imprinting and in tumorigenesis (for review: Millar et al.: Five not four: History and significance of the fifth base. In: The Epigenome, S. Beck and A. Olek (eds.), Wiley-VCH Publishers Weinheim 2003, pp. 3-20). The identification of 5-methylcytosine as a component of genetic information is thus of considerable interest. A detection of methylation is difficult, of course, since cytosine and 5-methylcytosine have the same base-pairing behavior. Many of the conventional detection methods based on hybridization thus cannot distinguish between cytosine and methylcytosine. In addition, information of methylation is completely lost in a PCR amplification.

The conventional methods for methylation analysis operate essentially according to two different principles. In the first one, methylation-specific restriction enzymes are used, and in the second one, there occurs a selective chemical conversion of unmethylated cytosines to uracil (so-called bisulfite treatment, see, e.g.: DE 101 54 317 A1; DE 100 29 915 A1). The DNA that has been pretreated enzymatically or chemically is then amplified for the most part and can be analyzed in different ways (for review: WO 02/072880 p. 1 ff). Therefore, methods which can detect methylation in a sensitive and quantitative manner are of great interest. This is true due to the important role of cytosine methylation in the emergence of cancer, particularly with respect to diagnostic applications. Of particular importance are methods which permit detection of deviant methylation patterns in body fluids, e.g., in serum. Unlike unstable RNA, DNA is often encountered in body fluids. The DNA concentration in blood in fact is increased in destructive pathological processes such as cancer disorders. A diagnosis of cancer by means of a methylation analysis of tumor DNA found in body fluids is thus possible and has in fact been described many times (see e.g.: Palmisano et al.: Predicting lung cancer by detecting aberrant promoter methylation in sputum. Cancer Res. 2000 Nov. 1; 60 (21): 5954-8). A problem here, however, consists of the fact that in body fluids, in addition to the DNA with the methylation pattern typical of disease, there is also found a large quantity of DNA of identical sequence, but of another methylation pattern. The diagnostic methods must thus be able to detect small quantities of specifically methylated DNA against an intense background of DNA of the same sequence but of another methylation pattern.

Common methods for sensitive detection are conducted via a PCR amplification. One method is so-called methylation-sensitive PCR ("MSP"; Herman et al.: Methylation-specific PCR: a novel PCR assay for methylation status of CpG islands. Proc Natl Acad Sci USA. 1996 Sep. 3; 93 (18): 9821-6). Here, primers are used which specifically bind only at positions of the bisulfite-treated sequence that were previously either methylated (or in the opposite approach: unmethylated). A comparable sensitive method is the so-called "heavy methyl" method. Here, a specific amplification of only the originally methylated (or unmethylated) DNA is achieved by use of methylation-specific blocker oligomers (for review: WO 02/072880). Both MSP and heavy methyl can be applied as quantifiable real-time variants. This makes possible the detection of the methylation state of a few positions directly in the course of the PCR without the need for a subsequent analysis of the products ("MethyLight"—WO 00/70090; U.S. Pat. No. 6,331,393). One embodiment of this is the "Taqman" method. This technique uses probe molecules which bear a fluorescent-dye/quencher pair. The probes hybridize in a sequence-specific manner to the amplified products and are decomposed in the course of the next amplification cycle due to the exonuclease activity of the polymerase. A detectable fluorescent signal arises due to the separation of quencher and dye (see, e.g., Eads et al.: MethyLight: a high-throughput assay to measure DNA methylation. Nucleic Acids Res. 2000 Apr. 15; 28(8): E32). Another MethyLight embodiment is the so-called LightCycler method. In this case, two different probes are utilized, which hybridize to the amplified product in direct proximity to one another, and then produce a detectable signal via fluorescence-resonance energy transfer (FRET).

The applicability of this real-time method for methylation analysis, of course, is limited. This is true particularly with respect to specificity, sensitivity and reaction rate. Based on the special biological and medical importance of cytosine methylation, however, there is a great technical need for the development of higher performing methods for methylation analysis. Such a method is described in the following. Here, probes and primers are joined together so that the hybridization of the probes to the target sequence can be produced intramolecularly. The method according to the invention permits an effective and rapid detection and thus makes possible a very sensitive and very specific methylation analysis.

A method for mutation analysis that is similar to the method according to the invention has already been described under the name "Scorpion" (see, e.g.: Whitcombe et al.: Detection of PCR products using self-probing amplicons and fluorescence. Nat Biotechnol. 1999 August; 17(8): 804-7; Thelwell et al.: Mode of action and application of Scorpion primers to mutation detection. Nucleic Acids Res. 2000 Oct. 1; 28(19): 3752-61; U.S. Pat. No. 6,326,145; U.S. Pat. No. 6,365,729; US 2003 0087240 A1). The Scorpion method is applicable in different embodiments. The intramolecular binding of the probe, of course, is common to all methods. In the so-called "hairpin loop" variant, the Scorpion primers bear at the 5'-end a specific probe sequence, which is present in a special hairpin loop configuration. A fluorescent dye and a quencher which are found at the ends of the probe sequence are placed in direct spatial proximity to one another by the hairpin formation. The probe and the primer sequence are joined by means of a linker, which bears a so-called PCR stopper. If, after one round of amplification, the double strand that has been formed is separated, then the probe binds intramolecularly to the elongated primer sequence of the same strand. This hybridization brings about the opening up of the hairpin, so that fluorescent dye and quencher are separated and thus a signal can be detected. The PCR stopper prevents a "read-through" of the polymerase within the PCR and thus avoids false-positive signals (see: Thelwell et al. 2000, loc. cit., particularly FIG. 1, p. 3753).

Another Scorpion variant is the so-called "duplex" method. The probe sequence is not present in a hairpin structure here, but rather forms a duplex with another oligonucleotide. Thus a fluorescent dye is bound at the 5'-end of the probe sequence, while the other oligonucleotide bears a quencher at the 3'-end. The quencher and dye are found in direct spatial proximity due to the duplex formation. If, after one round of amplification, the double strands are separated, then the probe binds intramolecularly to the elongated primer sequence of the same strand. Fluorescent dye and quencher are separated, so that a signal can be detected (Solinas et al.: Duplex Scorpion primers in SNP analysis and FRET applications. Nucleic Acids Res. 2001 Oct. 15; 29(20): E96). In addition, duplex variants are also described, in which the probes bear two dyes, and in which the signal is formed via a fluorescence-resonance energy transfer (see: Solinas et al. 2001, loc. cit., particularly p. 7 f and p. 6 FIG. 5). An advantage of the duplex method in comparison to the above-described hairpin method consists of the fact that a more intense fluorescent signal arises in the activated form due to the complete separation of quencher and dye. In addition, duplex Scorpion primers are simpler to synthesize and are less expensive than the corresponding hairpin primers (see: Solinas et al. 2001, loc. cit. p. 8 f).

Additional Scorpion variants have been described in detail in U.S. Pat. No. 6,326,145 and in US Patent Application 2003 0087240.

The Scorpion methods have several advantages when compared with conventional real-time PCR methods. This is true particularly with respect to the reaction rate. Thus the Scorpion probes hybridize intramolecularly to the target sequence and are the basis for one-molecule kinetics. In contrast, in the Taqman method, the binding of the probes takes place according to two-molecule kinetics, while in the LightCycler method, it takes place according to three-molecule kinetics. In the LightCycler method, an enzymatic degradation of the probe is also necessary, before a signal can be detected. Rapid PCR cycles, as are necessary, e.g., for high-throughput analyses, are thus possible only to a limited extent. It could be shown correspondingly that the Scorpion method is more efficient, particularly under rapid cycling conditions than the conventional real-time methodology (Thelwell et al. 2000, loc. cit.) Another advantage of the Scorpion method lies in its particular specificity. Therefore, by shortening the probe sequence, the specificity can be increased so that a single erroneous base pairing can be detected. A corresponding increase in specificity is not possible in the case of the conventional real-time variants. Shortened probes in such cases instead lead to a reduced specificity, since the probability of binding to nonspecific PCR products is increased (see: Thelwell et al. 2000, loc. cit., p. 3760).

The application of the Scorpion method to methylation analyses is described for the first time in the following. Based on the special biological and medical importance of cytosine methylation and based on the disadvantages of the known methods, the revelation of this advantageous new technology represents an important technical advance. In addition to the advantages of the Scorpion method which are already known from mutation analysis, the application of the Scorpion methodology in methylation analyses is associated with additional advantages. For example, a sensitive and specific methylation analysis is possible with the conventional PCR method only in the case of sequences which contain several co-methylated cytosine positions. In contrast, the method according to the invention in certain embodiments requires a smaller number of co-methylated positions. The Scorpion method in this case is more independent of sequence and thus has a broader field of application than the comparable known PCR method ("heavy methyl method", see below). The use of two Scorpion primers leads to additional particular advantages. Thus, methylation and mutations can be simultaneously investi-gated. Also, the use of two Scorpion primers permits an internal quantification (see below).

DESCRIPTION

The method according to the invention permits a sensitive detection of cytosine methylations. It is carried out in the following five steps:
1) the DNA to be investigated is reacted with a chemical or with an enzyme so that 5-methylcytosine remains unchanged, while unmethylated cytosine is converted to uracil or to another base which differs from cytosine in its base pairing behavior,
2) the pretreated DNA is amplified by means of a polymerase and at least one primer, whose 5'-end is joined with a probe via a linker,
3) the primer extension product is separated from the matrix strand,
4) the probe hybridizes intramolecularly to the primer extension product, whereby the hybridization occurs as a function of the methylation state of the DNA,
5) a detection is made of whether a hybridization of the probe has occurred.

In the first step of the method according to the invention, the DNA to be investigated is reacted with a chemical or with an enzyme so that 5-methylcytosine remains unchanged, while unmethylated cytosine is converted to uracil or to another base which differs from cytosine in its base-pairing behavior. The DNA to be investigated thus can originate from different sources depending on the diagnostic or scientific objective. For diagnostic objectives, tissue samples are preferably used as the initial material, but body fluids, particularly serum, can also be used. It is also possible to use DNA from sputum, stool, urine, or cerebrospinal fluid. Preferably, the DNA is first isolated from the biological specimen. The DNA is extracted according to standard methods, from blood, e.g., with the use of the Qiagen UltraSens DNA extraction kit. The isolated DNA can then be fragmented, e.g., by reaction with restriction enzymes. The reaction conditions and the enzymes that can be employed are known to the person skilled in the art and result, e.g., from the protocols supplied by the manufacturers. Then the DNA is chemically or enzymatically converted. A chemical conversion by means of bisulfite is preferred. The bisulfite conversion is known to the person skilled in the art in different variations (see, e.g.: Frommer et al.: A genomic sequencing protocol that yields a positive display of 5-methylcytosine residues in individual DNA strands. Proc Natl Acad Sci USA. 1992 Mar. 1; 89(5): 1827-31; Olek, A modified and improved method for bisulphite based cytosine methylation analysis. Nucleic Acids Res. 1996 Dec. 15; 24(24): 5064-6; DE 100 29 915; DE 100 29 915*). The bisulfite conversion is most preferably conducted in the presence of denaturing solvents, e.g., dioxane, and a radical trap (see: DE 100 29 915). In another preferred embodiment, the DNA is not chemically converted, but rather enzymatically converted. This is conceivable e.g., due to the use of cytidine deaminases; unmethylated cytidines react more rapidly than methylated cytidines. A corresponding enzyme has been recently identified (Bransteitter et al.: Activation-induced cytidine deaminase deaminates deoxycytidine on single-stranded DNA but requires the action of RNase. Proc Natl Acad Sci USA. 2003 Apr. 1; 100(7): 4102-7).

*sic; the number is repeated—Trans Note

In the second step of the method according to the invention, the pretreated DNA is amplified by means of a polymerase and at least one primer. Different possibilities are known to the person skilled in the art for this purpose, e.g., the use of isothermal amplification methods. Of course, polymer chain reactions (PCR) are preferred. Various embodiments are thus conceivable, each depending on the structure of the primers. It is common, of course, to all embodiments, that the 5'-end of at least one of the primers is joined to a probe via a linker. The entire sequence of primer, linker and probe—independent of the secondary structure of the probe—is designated below as the Scorpion primer. "Primer", in contrast, designates only the primer sequence of the Scorpion primer. Either the probe or the primer sequence must be methylation-specific for a methylation-specific detection. For example, it is possible to amplify originally methylated and unmethylated DNA in the same way and to distinguish the two forms later by hybridization with a methylation-specific probe. And vice versa, it is also possible to amplify only one type of DNA and to detect it later with a nonspecific probe. If a high specificity is required, then, of course, methods are preferred in which both the amplification as well as the detection are methylation-specific.

A methylation-specific amplification can be achieved in different ways. In a preferred embodiment, the PCR takes place with the use of primers which bind specifically only to positions of the unconverted sequence which were previously methylated (or in the reverse approach: unmethylated). This method is known under the name methylation-sensitive PCR (MSP). Here, primers which contain at least one CG dinucleotide are used; preferred are primers which bear at least three CG positions, at least one of which is localized at the 3'-end. Correspondingly, TG or CA dinucleotides are necessary for the amplification of unmethylated sequences or of the counterstrands. The precise technical information for conducting an MSP are known to the person skilled in the art (see: Herman et al.: Methylation-specific PCR: a novel PCR assay for methylation status of CpG islands. Proc Natl Acad Sci USA. 1996 Sep. 3; 93(18): 9821-6; U.S. Pat. No. 5,786,146; U.S. Pat. No. 6,017,704; U.S. Pat. No. 6,200,756).

Another preferred embodiment for the methylation-specific amplification is the "heavy methyl" method. In this case, at least one methylation-specific blocker oligomer is utilized, which binds to a CG (or TG or CA) dinucleotide and thus prevents the amplification of the background DNA. By selecting the polymerase or by modifying the blocker oligomers, the embodiment can be designed in such a way that a degradation or an extension of the blockers is minimized. Precise technical information for conducting the amplification is known to the person skilled in the art (WO 02/072880).

The methylation-specific and the non-methylation-specific amplifications can be combined according to the invention with different linkers and probe elements. It is common, of course, to all embodiments, that the 5'-end of at least one of the primers is joined to a probe sequence via a linker. Information on length and the structure of the linker are found from the prior art. In particular, it must be assured that the probe is not amplified. This can be achieved by means of different designs which are known to the person skilled in the art (EP 0 416,817; U.S. Pat. No. 5,525,494; US 2003 0087240). In a preferred embodiment, the linker contains a PCR blocker, which prevents the primer extension on the counterstrand. Particularly preferred are hexaethylene glycol (HEG) monomers. Alternatively, the linker can contain 2-O-alkyl-RNA. The use of oligonucleotides which are partially combined with one another in the 5'-5' direction is also possible (see: US 2003 0087240).

In addition, the Scorpion primers are constructed in such a way that the probe can bind intramolecularly to an extension product of the primer. According to the invention, the hybridization of the probe takes place as a function of the methylation state of the original DNA. This means that hybridization occurs only if the matrix DNA was present originally methylated or else unmethylated at the positions to be investigated. Such a methylation-specific detection can be conducted in different ways. If the amplification has already taken place in a methylation-specific manner, then a non-methylation-specific probe may be sufficient. A hybridization of the probe then occurs only if a (methylation-specific) amplified product has formed. According to the invention, the use of a methylation-specific probe is preferred, of course. This probe binds either only to the originally methylated or originally unmethylated DNA. Correspondingly, the probe contains at least one methylation-specific CG, TG or CA dinucleotide. One to three corresponding dinucleotides are preferred. The probe sequence is preferably between 6 and 50 nucleotides long, particularly preferred between 10 and 40 nucleotides long, and most preferred between 15 and 30 nucleotides long. The probe may contain nucleic acid analogs such as peptide nucleic acids (PNAs) or 2'-O-alkyl-RNA. Further technical information relative to length and structure of the probes is found in U.S. Pat. No. 6,326,145 and in US Patent Application 2003 0087240.

The probe also bears at least one label, by means of which a detection can be made of whether a hybridization has occurred. Various signal systems are known to the person skilled in the art for this purpose. Thus, among other things, fluorescent dye/quencher pairs, intercalating dyes and dye pairs, which produce signals via fluorescence-resonance energy transfer (FRET) can be used. The use of systems which also make possible a binding of amplified products to a solid phase is also conceivable. These and other examples, which can also be used for methylation analysis and thus are part of this invention, are described in detail and with additional citations in U.S. Pat. No. 6,326,145 and in US Application 2003 0087240 (in particular, [0018]; [51] ff).

The signal systems preferably consist of two components. These are designed in one embodiment such that a signal is formed only if the two components are spatially separated from one another. And vice versa, it is also possible that a signal is generated only if the two components are found in direct spatial proximity to one another. In both embodiments, the components are provided either by the same molecule or by different molecules. By means of different secondary structures for the probe, the components can be kept in the necessary spatial configuration. Such configurations include, e.g., hairpins, loops, pockets, branches, elbows and stems. Correspondingly, the prior art includes a multiple number of possible embodiments (see U.S. Pat. No. 6,326,145; US 2003 0087240, in particular [52] ff). These embodiments can be applied also to methylation analysis and are thus part of this invention.

In a preferred embodiment, fluorescent dye/quencher pairs are used. Corresponding pairs are known to the person skilled in the art (see, e.g., US 2003 0087240 [0020] with further citations). In a particularly preferred variant, both the quencher as well as the dye are bound to the probe and are found in the inactive form in direct spatial proximity to one another due to a hairpin formation (see: Thelwell et al. 2000 loc. cit.). Precise technical information on usable hairpin structures belong to the prior art (U.S. Pat. No. 6,326,145; US 2003 0087240).

In another preferred embodiment, the Scorpion primer bears two signal components, which are spatially separated from one another in the inactive form and which are brought together in spatial proximity to one another by the hybridization of the probe to a primer extension product. In a particularly preferred variant, the signal components in the active form generate a signal via a fluorescence-resonance energy transfer. Here, the first component is found in the 3' region and the second component is found in the 5' region of the Scorpion primer.

In another particularly preferred embodiment, the signal components are bound to different molecules and are found in spatial proximity to one another in the inactive form. This is possible, e.g., by using another oligonucleotide, which forms a duplex with the probe in the inactive form. In this case, the probe bears a fluorescent dye at its 5' end, while the other oligonucleotide bears a quencher at its 3' end. Instead of an oligonucleotide, oligomers of nucleic acid analogs, e.g., peptide nucleic acid oligomers can also be used (see: Solinas et al. loc. cit.; U.S. Pat. No. 6,326,145; US 2003 0087240).

In other particularly preferred embodiments, the quencher is also bound to another oligonucleotide which forms a special spatial structure with the probe when it is in the inactive form. The probe bears two dyes in this case. As soon as the probe and the other oligonucleotide are separated from one another, a signal is formed between the two dyes by means of a fluorescence-resonance energy transfer. Instead of an oligonucleotide, oligomers of nucleic acid analogs, e.g., peptide nucleic acid oligomers can also be used (see: Solinas et al. 2001, loc. cit., particularly p. 7 f and p. 6 FIG. 5).

A fifth particularly preferred embodiment is similar to the LightCycler method and uses an additional, dye-labeled molecule. A particular spatial structure between the other molecule and the probe is not necessary here. Again, the signal is formed by means of a fluorescence-resonance energy transfer. In the active form, the other molecule binds to the amplified product in addition to the probe, so that the two dyes end up in direct proximity to one another, and thus a signal is generated. An oligonucleotide or an oligomer of nucleic acid analogs is preferably used as the other molecule. The specificity of the detection reaction can be increased, if the oligonucleotide or oligomer sequence is methylation-specific. i.e., at least one CG (or TG or CA) dinucleotide. The sequence is preferably 15-30 nucleotides long. Further technical information for the person skilled in the art can be taken from the known LightCycler method.

All of the above-described embodiments can be carried out with the use of only one Scorpion primer in addition to a conventional primer. It is preferred according to the invention, however, also if both the forward—as well as the reverse_primers are present in the Scorpion form. Such a combination may be associated with a multitude of advantages. Thus, a first particularly preferred embodiment makes possible an increase in the sensitivity of the methylation analysis. In this way, both Scorpion primers generate the same signals in the active form. The probes hybridize to different, co-methylated positions of the DNA. The signals of the two Scorpion primers are additive, so that the signal intensity is increased. Conversely, in a second particularly preferred embodiment, the specificity of the detection reaction can be increased. In this case, the Scorpion primers bear different signal components. Here also, the probes hybridize to different, co-methylated positions of the DNA. However, a positive signal is produced only if the two signals occur simultaneously. A third particularly preferred embodiment permits an exact internal quantification of the methylation analysis. In this case, one of the Scorpion primers is used for the methylation analysis and the other Scorpion primer is used for the determination of the total quantity of DNA. This is possible, e.g., if a non-methylation-specific amplification occurs and the two Scorpion primers bear different signal components. The probe of the first Scorpion primer then hybridizes to methylation-specific positions, as described above, while the probe of the second Scorpion primer binds to non-methylation-specific positions. By means of the signal generated by the second Scorpion primer, the total quantity of DNA can then be determined, while the signal of the first Scorpion primer indicates the quantity of methylated (or unmethylated) DNA. The quantity of methylated DNA can be determined exactly from the two signals. A fourth particularly preferred embodiment makes possible simultaneously a methylation analysis and a mutation analysis or an allele discrimination. For this purpose, the first Scorpion primer is used for the methylation analysis (see above) and the second Scorpion primer is used for the mutation analysis (or allele discrimination). In this case, the two Scorpion primers bear different signal components. The probe sequence of the second Scorpion primer is specific for a specific mutation (or a specific allele). Then the methylation state as well as the presence of a mutation can be concluded from the generated signals.

As already mentioned above, different methylation-specific or non-methylation-specific amplification methods with different linkers and different probe systems can be combined. One or two Scorpion primers can be utilized simultaneously. A plurality of embodiments which are suitable for methylation analysis results thereby, and these are also to be regarded according to the invention. How these methods are to be conducted can be found from this Application in combination with the prior art. Preferred reaction conditions of the invention will be described in more detail in the following. As is known by the person skilled in the art, the optimal reaction conditions may vary, however, for several embodiments.

It is not necessary for the method according to the invention to utilize Scorpion primers exclusively. Rather, it is sufficient, if only a small proportion of Scorpion primers is used along with conventional primers of the same sequence. The optimal ratio between the two types of primers depends on the structure of the special assay and can easily be determined experimentally. When suitable signal systems are used (e.g different fluorescent dyes), it is also possible to investigate several sequences simultaneously by the use of different Scorpion primers (see, e.g., Thelwell et al. 2000 loc. cit.; US 2003 0087240). The Scorpion primers can be added to the reaction batch at different times in the course of an amplification reaction. Thus, it may be sufficient if the Scorpion primers participate only in the last amplification cycle. This is true, e.g., for the case when an end-point analysis is to be conducted (see: Solinas et al. 2001, loc. cit. p. 6). Preferably, the Scorpion primers are present, of course, at the beginning of the amplification. This particularly applies to real-time applications. The amplification is preferably conducted by means of a PCR. The person skilled in the art knows how reagents, concentrations and temperature cycles can be determined.

In the third step of the method according to the invention, the primer extension product is separated from the matrix strand. This is necessary in order to make possible a binding of the probe to the primer extension product. This separation is preferably conducted by means of an increase in temperature. In a PCR, this increase in temperature can be part of the usual temperature cycle.

In the fourth step of the method according to the invention, the probe hybridizes to the primer extension product, whereby the hybridization will occur as a function of the methylation state of the original DNA. This means that hybridization occurs only if the matrix DNA at the positions to be investigated was present originally methylated or else unmethylated. If a non-methylation-specific amplification occurs, then the methylation-specific hybridization must be assured by the sequence of the probe. In the case of a methylation-specific amplification and the use of a non-methylation-specific probe, a binding then results only when a (methylation-specific) product has formed in general (see above). If the reaction is produced by means of two Scorpion primers, then the hybridization of the probe of the second Scorpion primer takes place independently of the methylation state, e.g., if the total amount of DNA is determined and in addition to the methylation analysis, a mutation analysis is also conducted (see above).

In the fifth step of the method according to the invention, a detection is made of whether a hybridization has occurred. In this case, the detection is made as a function of signal formation produced according to the prior art.

The person skilled in the art knows that steps 2 to 5 of the method according to the invention can be repeated several times. This particularly applies to real-time applications.

As has already been mentioned several times, the method according to the invention can be applied to multiple embodiments. Several preferred embodiments are described in more detail in the following. The person skilled in the art can derive precise technical information for designing this method from the prior art in combination with this Application. Nevertheless, the method according to the invention is not limited to the variants presented below. Rather, the embodiments of Scorpion technology for methylation analysis which are disclosed elsewhere are also applicable and are thus a part of this invention (see particularly: Thelwell et al. loc. cit.; Solinas et al. loc. cit.; U.S. Pat. No. 6,326,145; US 2003 0087240, particularly [52] ff).

Figure 5:
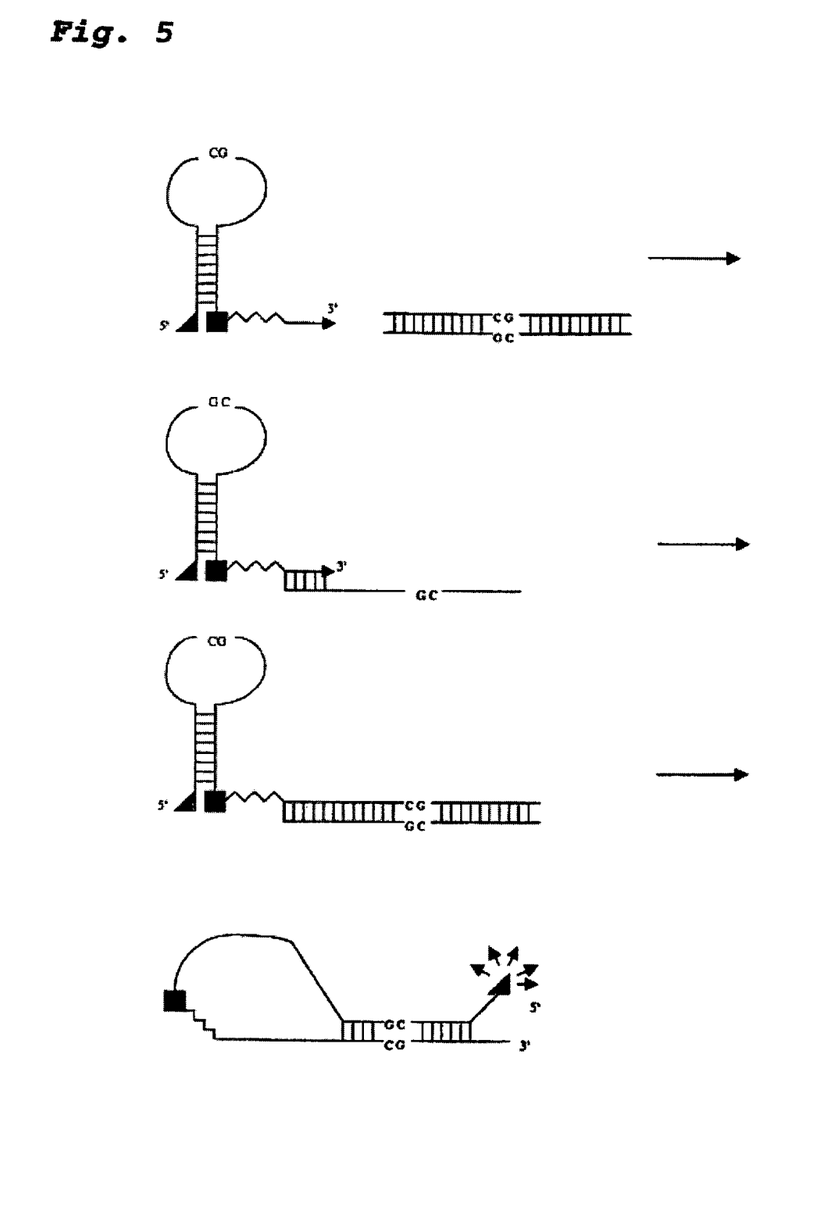

A first preferred embodiment is designated in the following as a "methyl hairpin". The amplification of the chemically or enzymatically pretreated DNA in this case is produced by means of a non-methylation-specific PCR. Correspondingly, primers are utilized, which bind in the same way to originally methylated and to originally unmethylated DNA. The primers thus do not contain CG dinucleotides and only those TG and CA dinucleotides that correspond to positions that were already present in this sequence prior to the conversion. A Scorpion primer and a conventional PCR primer are preferably utilized as the pair of primers. The linker of the Scorpion primer preferably contains hexaethylene glycol (HEG) monomers in order to prevent an amplification of the probe. Other possibilities are known to the person skilled in the art for how to design the linker element (EP 0 416,817; U.S. Pat. No. 5,525,494; US 2003 0087240). The probe element of the Scorpion primer forms a hairpin structure. The probe sequence is preferably between 6 and 50 nucleotides long, particularly preferred between 10 and 40 nucleotides long, and most preferred between 15 and 30 nucleotides long. The probe in this case may contain nucleic acid analogs such as peptide nucleic acids (PNAs) or 2'-O-alkyl-RNA. Precise technical information on length and structure of usable hairpin structures belong to the prior art (U.S. Pat. No. 6,326,145; US 2003 0087240). The probe sequence is methylation-specific, i.e., it bears at least one CG dinucleotide or methylation-specific TG and CA dinucleotides, respectively. One to three corresponding dinucleotides are preferred. The probe also bears a pair comprising a fluorescent dye and a quencher, which are found in direct spatial proximity due to the hairpin formation. An extension of the Scorpion primer and then a thermal separation of the extended primer from the matrix strand occur in the course of the PCR. The probe of the Scorpion primer then binds intramolecularly to the extended primer as a function of the methylation state. A fluorescent signal is formed by the separation of dye and quencher. The signal can be detected in different ways according to the prior art. It is sufficient for the method according to the invention to utilize only a small proportion of Scorpion primers along with conventional primers of the same sequence (see above). With the use of suitable signal systems, it is possible to investigate several sequences simultaneously with the use of different Scorpion primers. A methyl hairpin method is described in Example 1. Example 2 shows a comparison between the MethyLight and the methyl hairpin technology. The course of a methyl hairpin reaction is shown in a rough schematic diagram in FIG. 5.

A second preferred embodiment is designated in the following as an "MSP methyl hairpin". The amplification of the chemically or enzymatically pretreated DNA in this case is produced by means of a methylation-specific PCR. Correspondingly, primers are utilized, which preferably bind either to the originally methylated or to the originally unmethylated DNA. The primers thus contain CG dinucleotides or methylation-specific TG or CA dinucleotides. Preferably the primers bear at least three corresponding dinucleotides, at least one of which is localized at the 3'-end. A Scorpion primer and a conventional PCR primer are preferably utilized as the pair of primers. The linker and the probe are constructed as in the methyl hairpin method (see above). The probe preferably provides a methylation-specific sequence, i.e., it bears at least one CG dinucleotide or methylation-specific TG or CA dinucleotide, respectively. One to three corresponding dinucleotides are preferred. Since the amplification is already produced in a methylation-specific manner, it is also possible to utilize a non-methylation-specific probe. The signal is generated as in the case of the methyl hairpin method via a fluorescent dye/quencher pair (see above).

A third preferred embodiment is designated in the following as a "heavy methyl hairpin". The amplification of the chemically or enzymatically pretreated DNA in this case is produced by means of a methylation-specific heavy-methyl PCR (see above). For this purpose, non-methylation-specific primers are utilized, i.e., primers which bind in the same way to originally methylated and to originally unmethylated DNA. The primers thus do not contain CG dinucleotides and only those TG and CA dinucleotides that correspond to positions that were already present in this sequence prior to the conversion. The methylation-specific amplification is assured by the use of at least one methylation-specific blocker oligomer. The blocker binds to a CG (or to a methylation-specific TG or CA) dinucleotide and thus prevents the amplification of the background DNA. By selecting the polymerase or by modifying the blocker oligomers, the embodiment can be designed in such a way that a degradation or an extension of the blockers is minimized. A Scorpion primer and a conventional PCR primer are preferably utilized as the pair of primers. The linker and the probe are constructed as in the methyl-hairpin method (see above). The probe preferably provides a methylation-specific sequence, i.e., it bears at least one CG dinucleotide or methylation-specific TG or CA dinucleotide, respectively. One to three corresponding dinucleotides are preferred. In a particularly preferred embodiment, the heavy methyl hairpin assay uses the same methylation-specific dinucleotides for the blocking and for generating the signal. In this way, the number of dinucleotides necessary for analysis is reduced, so that the heavy methyl hairpin method may have a broader applicability than the heavy methyl method. An increased specificity is also achieved. Since the amplification is produced in a methylation-specific manner, it is possible to use a non-methylation-specific probe. The signal is generated as in the case of the methyl hairpin method via a fluorescent dye/quencher pair (see above). A heavy methyl hairpin method is described in Example 3.

Figure 6:
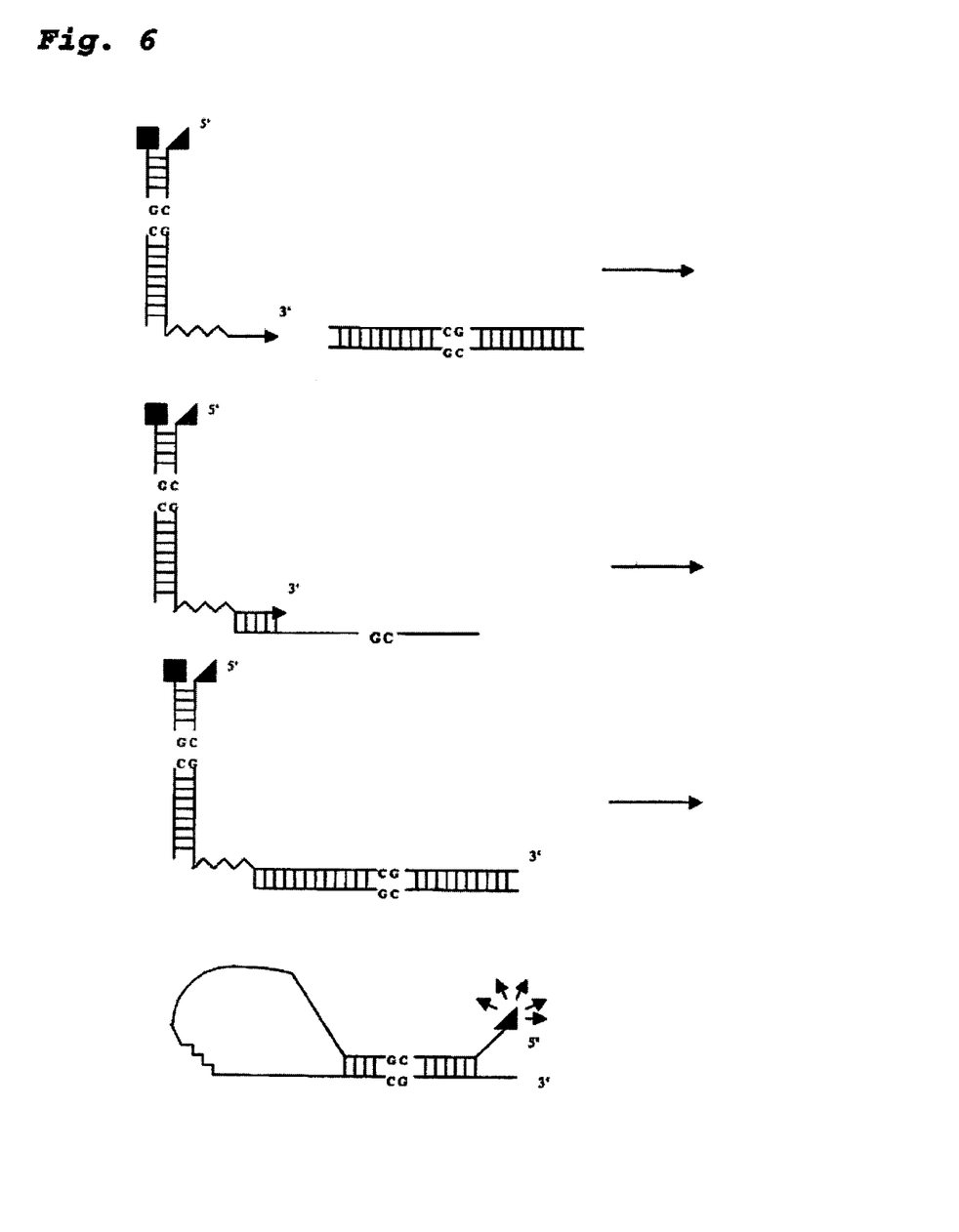

A fourth preferred embodiment is designated "methyl-duplex" in the following. This variant is distinguished from the above-described methyl hairpin variant only by the probe element. In the methyl duplex method, dye and quencher are bound to different molecules and are found in spatial proximity to one another in the inactive form. This is possible, e.g., by use of another oligonucleotide, which forms a duplex with the probe in the inactive form. Instead of an oligonucleotide, other oligomers of nucleic acid analogs, e.g., peptide nucleic acid oligomers can also be used. (See: Solinas et al. loc. cit.; U.S. Pat. No. 6,326,145; US 2003 0087240). The course of a methyl hairpin reaction is shown in a rough schematic diagram in FIG. 6.

A fifth preferred embodiment is designated in the following as an "MSP methyl duplex". This variant is distinguished from the above-described MSP methyl hairpin variant only by the probe element. This element in turn forms a special spatial structure, i.e., a duplex, with another oligomer (see above).

A sixth preferred embodiment is designated in the following as "heavy methyl duplex". This variant corresponds to a combination of the heavy methyl hairpin with a probe element which forms a special spatial structure, i.e., a duplex, with another oligomer (see above).

A seventh particularly preferred embodiment involves a quantitative "methyl hairpin" assay. This embodiment corresponds to the "methyl hairpin assay" in which a second Scorpion primer is utilized. In this case, an internal quantification is possible. The probe of the second Scorpion primer is non-methylation-specific and binds to the amplified product independent of the methylation state. By means of the signal generated in this way, the total quantity of DNA can then be determined, while the signal of the first Scorpion primer produces the quantity of methylated (or unmethylated) DNA. The quantity of methylated DNA can be determined exactly from the two signals.

Another aspect of the invention consists of the use of all embodiments according to the invention. If disease-specific cytosine positions are investigated, then the method according to the invention is particularly suitable for the diagnosis or prognosis of cancer disorders or other diseases associated with a change of methylation state. These include, among others, CNS malfunctions; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as a consequence of an abnormality in the development process; malfunction, damage or disease of the skin, the muscles, the connective tissue or the bones; endocrine and metabolic malfunction, damage or disease; headaches or sexual malfunction. The method according to the invention is also suitable for predicting undesired drug effects, for establishing a specific drug therapy (personalized medicine) and for monitoring the success of a drug therapy. Another application is distinguishing cell types or tissues and investigating cell differentiation.

The subject of the invention is also the use of Scorpion primers for methylation analysis and for the detection or for the prognosis of the above-named disorders associated with a change in the methylation state. Another subject of the invention is the use of Scorpion primers for predicting undesired drug effects, for establishing a specific drug therapy (personalized medicine) and for monitoring the success of a drug therapy. The subject of the invention is also the use of Scorpion primers for differentiating cell types or tissues and for investigation of cell differentiation. A Scorpion primer is thus understood to be a primer which is bound at its 5'-end to a probe sequence via a linker (see above).

Finally, the subject of the present invention is also a kit, consisting of at least one Scorpion primer, a polymerase and the necessary reagents for a PCR.

EXAMPLES

Example 1: Quantification of Methylated DNA of the brca1 Gene with a Methyl Hairpin Real-Time PCR Assay A bisulfite-treated fragment of the human brca1 was amplified (Genebank Accession: L78833.1, nt 3538-nt 3666; Seq ID-7). Human DNA from peripheral blood cells (Roche Diagnostics) and comprising methylated human DNA (Serologicals) was utilized as the matrix. Both types of DNA were treated with a bisulfite solution (Olek et al. 1996, loc. cit.). In this way unmethylated cytosines were converted to uracil, while 5-methylcytosines remained unchanged. After the bisulfite treatment, the DNA concentration was determined by means of UV absorption (260 nm). The efficiency of the assay was investigated with the use of 10 ng, 1 ng and 0.1 ng of bisulfite-treated methylated matrix DNA. The reaction was conducted in a total volume of 20 µl with the use of a LightCycler apparatus. The reaction batch contained 10 µl of matrix DNA (see below for concentration data), 2 µl of the FastStart-LightCycler reaction mix for hybridization probes (Roche Diagnostics), 0.30 µmol/l forward primer (5'-GAAGtTGAtAGATGGGTATTtTTTGA-3'; Seq ID-1), 0.10 µmol/l reverse primer (5'-CCCCCTTCCTaATCCTCAa-3'; Seq ID-2), 0.5 µmol/l Scorpion primer (5'-FAM-GGCAGC-CTAGGTCGCGAGGGAAGGCTGCC-MR-HEG-CCCCCTTCCTaATCCTCAa-3'; probe element: Seq ID-6; primer element: Seq ID-8) und 2 mmol/l MgCl$_2$. The thermocycles began with an incubation at 95° C. for 10 minutes, followed by 55 cycles with the following steps: 95° C. for 10 seconds, 56° C. for 30 seconds und 72° C. for 10 seconds. The fluorescence was detected in each cycle prior to the annealing phase at 56° C.

Due to the identical base-pairing properties of uracil and thymine, those positions which correspond to the converted, unmethylated cytosines are designated with a lower-case "t" (or a lower-case "a" in the complementary strand). In contrast, the capital "T" (or "A" in the complementary strand) stands for thymine that is already present prior to the bisulfite treatment. The abbreviations in the primer sequences here and in the further examples stand for the following: FAM=fluorescein label; red640=LightCycler fluorescence label for channel F2; MR=methyl red label; HEG=hexaethylene glycol spacer; pho=phosphate modification; fluo=fluorescein.

Figure 1:
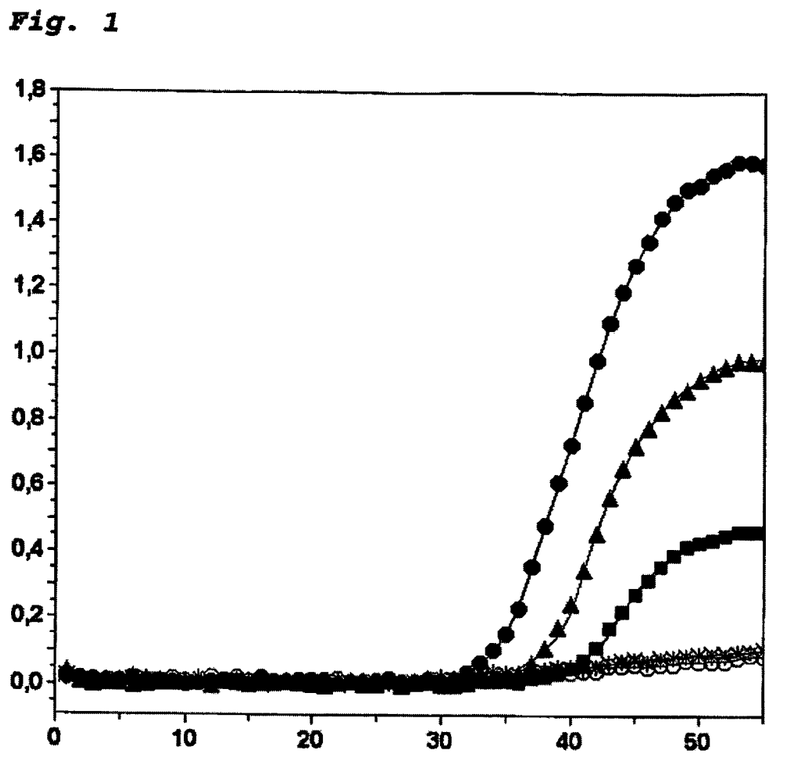
FIG. 1: Real-time amplification of the bisulfite-treated brca1 DNA by means of the methyl hairpin assay (Example 1). The Y-axis shows the fluorescent signal measured in each cycle (channel F1). The X-axis shows the number of cycles. The negative controls produce no signal: water (stars), 50 ng of genomic DNA (X's); 10 ng of unmethylated, bisulfite-treated DNA (open circles). The methylated, bisulfite-treated DNA is characterized by the filled circles (10 ng), filled triangles (1 ng) and filled squares (0.1 ng).

The results are shown in Table 1 and in FIG. 1. Table 1 shows the mean value for the threshold values of two repetitions calculated by the LightCycler software. No amplified products were produced in the negative controls (10 ng of unmethylated bisulfite-treated DNA; 50 ng of genomic DNA; water). The data show that a specific detection of the methylated, bisulfite-treated DNA of the brca1 gene is possible with the methyl hairpin assay. In the case of the bisulfite-treated, methylated matrix DNA, the PCR shows a linearity of at least three orders of magnitude (FIG. 1). The methyl hairpin assay can thus quantify methylated DNA on real-time PCR platforms.

Table 1: Efficiency of the brca1 methyl hairpin assay for the detection of methylated DNA. The threshold cycles were obtained with the LightCycler software from two repetitions (method: second derivative maximum).

| Quanity of bisulfite-treated matrix DNA (ng) | Threshold cycles for methyl hairpin |
|---|---|
| 10 | 34.9 |
| 1 | 37.9 |
| 0.1 | 40.8 |
| 0.0 | 0 |

Example 2: Comparison of a methyl-hairpin assay with a MethyLight assay for the methylation-specific detection of the brca1 amplicon in DNA mixtures of methylated and unmethylated, bisulfite-treated DNA The real-time PCR methods for the methyl hairpin and the MethyLight technologies were compared in the following. The quantity of originally methylated, bisulfite-treated DNA against a background of originally unmethylated, bisulfite-treated DNA was determined.

The PCR amplifications were conducted in a total volume of 20 µl with the use of a LightCycler apparatus (Roche Diagnostics). A bisulfite-treated DNA fragment of the human brca1 gene was amplified (nt 3538-nt 3666 in Genebank Accession No. L78833.1; Seq ID-7). The methyl hairpin reaction batch contained 10 µl of matrix DNA (see below for concentrations), 2 µl of the FastStart-LightCycler reaction mix for hybridization probes (Roche Diagnostics), 0.30 µmol/l forward primer (5'-GAAGtTGAtAGATGGGT-ATTtTTTGA-3'; Seq ID-1), 0.10 µmol/l reverse primer (5'-CCCCCTTCCTaATCCTCAa-3'; Seq ID-2), 0.5 µmol/l Scorpion primer (5'-FAM-GGCAGCCTAGGTCGC-GAGGGAAGGCTGCC-MR-HEG-CCCCCTTCCTaATC-CTCAa-3'; probe element: Seq ID-6; primer element: Seq ID-8) and 2 mmol/l MgCl$_2$. The MethyLight reaction batch contained 10 µl of matrix DNA, 2 µl of the FastStart-LightCycler reaction mix for hybridization probes (Roche Diagnostics), 0.30 µmol/l forward primer (5'-GAAGtTGA-tAGATGGGTATTtTTTGA-3'; Seq ID-1), 0.30 µmol/l reverse primer (5'-CCCCCTTCCTaATCCTCAa-3'; Seq ID-2), 0.25 µmol/l hybridization probe 1 (5'-GCGGAAttT-GAGAGGCGTA-fluo-3'; Seq ID-3) and hybridization probe 2 (5'-red640-GCGTTGTGAAtttTGGGGAG-pho-3'; Seq ID-4). The thermocycles began with an incubation at 95° C. for 10 minutes, followed by 55 cycles with the following steps: 95° C. for 10 seconds, 56° C. for 30 seconds and 72° C. for 10 seconds. The fluorescent signals were detected in each cycle prior to the annealing phase at 56° C.

The DNA was isolated from the same source as described in Example 1. A total quantity of 20 ng of bisulfite-treated DNA was utilized in each reaction. The fractions of methylated DNA amounted to 100%, 50% and 10%. This corresponds in absolute quantities to 20 ng (100%), 10 ng (50%) and 2 ng (10%) per reaction. Both assays were conducted in parallel in the same LightCycler apparatus with the same DNA mixtures. The fluorescent signals were detected in different channels. The methyl hairpin assay generated signals in channel F1 (520 nm). The signals of the MethyLight assay were detected in channel F2 (640 nm).

Figure 2:
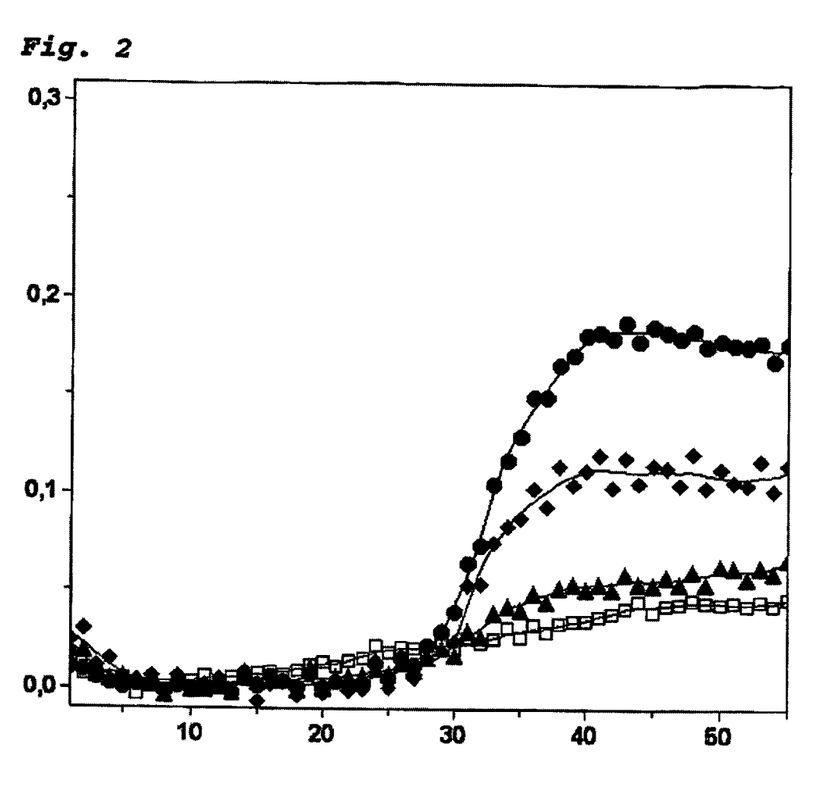
FIG. 2: Real-time amplification of the bisulfite-treated brca1 DNA by means of the MethylLight assay with the use of hybridization probes (Example 2). The Y-axis shows the fluorescent signal in channel F2 (640 nm). The measurement was made in each cycle (X-axis). The curves show 100% (filled circles), 50% (filled diamonds) and 10% methylated DNA (filled triangles) against a background of unmethylated DNA. In all, 20 ng of bisulfite-treated DNA were investigated in each batch. A signal could not be determined for 20 ng of unmethylated DNA (open squares).
Figure 3:
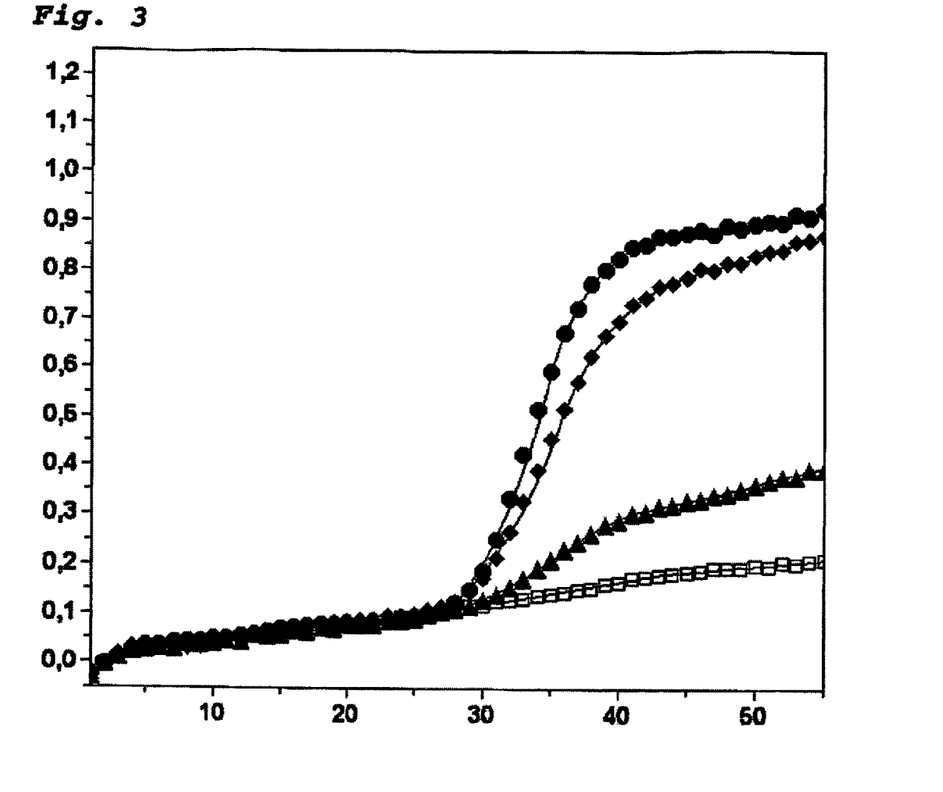
FIG. 3: Real-time amplification of the bisulfite-treated brca1 DNA by means of the MethylLoop* assay with the use of hybridization probes (Example 2). The Y-axis shows the fluorescent signal in channel F1 (520 nm). The measurement was made in each cycle (X-axis). The curves show 100% (filled circles), 50% (filled diamonds), and 10% methylated DNA (filled triangles) against a background of unmethylated DNA. In all, 20 ng of bisulfite-treated DNA were used in each batch. A signal could not be detected for 20 ng of unmethylated DNA (open squares).

The experimental data show that for all concentrations and with both assays, signals of methylated DNA can be obtained against a background of unmethylated DNA (FIGS. 2 and 3). Unmethylated, bisulfite-treated DNA produced no signals. The methyl hairpin assay generated higher signals in comparison to the MethyLight assay and permitted a better analysis. This is particularly true for the 10% samples. The signal of the MethyLight assay thus is 140% above the background signal, while the signal of the Scorpion assay is 180% higher. The results show that the methyl hairpin assay can detect at least 2 ng of methylated DNA against a background of 18 ng of unmethylated DNA. Therefore, it had a higher sensitivity than the MethyLight assay.

Example 3: Use of the Heavy Methyl Hairpin Assay for the Detection of Methylated DNA of the brca1 Gene with a 4000× Higher Background of Unmethylated DNA The assay described here combines the advantages of the heavy methyl and the methyl hairpin technologies. The use of methylation-specific blocker (heavy methyl) and methylation-specific detection with Scorpion primers (methyl hairpin) creates a novel real-time PCR technology for a sensitive detection of methylated DNA (heavy methyl hairpin).

The heavy methyl hairpin assay was conducted in a total volume of 20 µl with the use of a LightCycler apparatus (Roche Diagnostics). A bisulfite-treated DNA fragment of the human brca1 gene was amplified (nt 3538-nt 3666 in Genebank Accession No. L78833.1; Seq ID-7). The reaction mixture contained 10 µl of matrix DNA (see below for concentrations), 2 µl of the FastStart-LightCycler reaction mix for hybridization probes (Roche Diagnostics), 0.30 µmol/l forward primer (5'-GAAGtTGAtAGATGGGT-ATTtTTTGA-3'; Seq ID-1), 0.10 µmol/l reverse Primer (5'-CCCCCTTCCTaATCCTCAa-3'; Seq ID-2), 0.5 µmol/l Scorpion primer (5'-FAM-GGCAGCCTAGGTCGC-GAGGGAAGGCTGCC-MR-HEG-CCCCCTTCCTaATC-CTCAa-3'; probe element: Seq ID-6; primer element: Seq ID-8), 4 µmol/l blocker (5'-TAATCCTCAaCACTTCCCT-CACAACCT-pho-3'; Seq ID-5) und 2 mmol/l MgCl$_2$.

The thermocycles began with an incubation at 95° C. for 10 minutes, followed by 55 cycles with the following steps: 95° C. for 10 seconds, 56° C. for 30 seconds and 72° C. for 10 seconds. The fluorescent signals were detected in each cycle prior to the annealing phase at 56° C. The DNA mixtures were isolated from the same source as described in Example 1. The quantity of originally methylated, bisulfite-treated DNA amounted to 100 pg in each sample. The quantity of unmethylated background DNA varied each time. Ratios of methylated to unmethylated DNA of 1:1000 and 1:4000 were prepared by appropriate mixtures after the bisulfite treatment. Correspondingly, 100.1 ng (1:1000) or 400.1 ng (1:4000), respectively, resulted as absolute DNA quantities for the reactions. 100 pg of methylated DNA without unmethylated background were used as the positive control and 100 ng of unmethylated DNA were used as the negative control.

Figure 4:
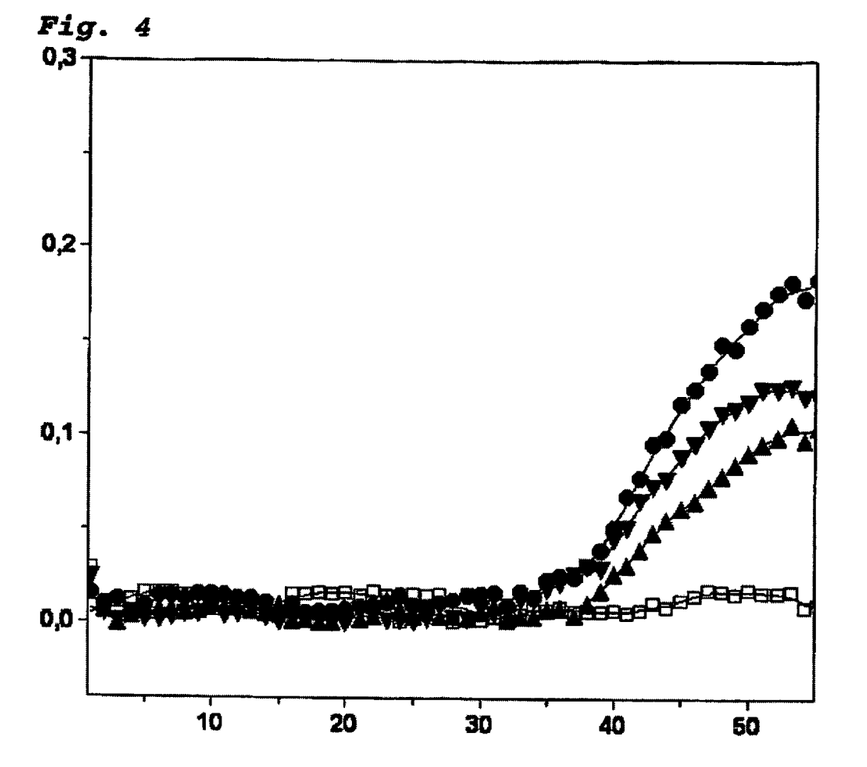

The results are shown in FIG. 4. 100 pg of methylated DNA could be detected with the heavy methyl hairpin assay in both relative sensitivities of 1:1000 and 1:4000. No signals were obtained for 100 ng of unmethylated DNA. In contrast, the positive controls with 100 pg of methylated DNA without the background of unmethylated DNA gave the strongest signal. The data show that the heavy methyl hairpin assay can assure a sensitive detection of methylated DNA against a 4000-fold background of unmethylated DNA.

Example 4: (Theoretical Example: Methylation Analysis of the GSTPi Gene by Scorpio* Real-Time Analysis (Heavy Methyl Hairpin Assay)

The following (bisulfite-treated) fragment of the GSTPi gene is amplified: CGGGAttAtttTTATAAGGtTCGGAG-GtCGCGAGGttTTCGtTGGAGTTTCGtCGtCGtA GTtTTCGttAttAG (SEQ ID NO: 9; nt 1845-nt 1924 in Genebank Accession No. AY324387). The PCR is conducted with the reaction conditions described above. The following sequences are used as primers: forward primer (GGGAttAtttTTATAAGGtT; SEQ ID NO: 10), reverse primer (TACTCACTaaTaaCKAAaACTaC; SEQ ID NO: 1), Scorpion primer (FAM-ggcagccGtTG-GAGtttCGtCGggct-gcc-DDQ-HEG-TACTCACTAATAACKAAAACTAC; SEQ ID NO: 12, 13), 4 µM blocking probe (CTAATAACaAAAACTACaACaACaAAACTCCAAC-PHO; SEQ ID NO: 14). Instead of the above-described standard Scorpio* primer, the following duplex Scorpio* primer can also be used: FAMGtTGGAGtttCGtCG-HEG-TACTCACTAATAACKAAAACTAC (Seq ID**; CGaC-GaaaCTCCAaC-DDQ; Seq ID NO: 15; NO: 16).

*sic; Scorpion?—Trans. note
**sic; no number is indicated-Trans. note

EXPLANATIONS TO FIGURES

*sic; MethyLight?—Trans. Note

FIG. 4: Sensitive detection of the brca1-DNA with the heavy methyl hairpin assay (Example 3). The Y-axis shows the fluorescent signal in channel F1 (640 nm). The measurement was made in each cycle (X-axis). Each time the determination was made with 100 pg of methylated DNA with the following quantities of unmethylated background DNA: without background DNA (filled circles), 100 ng (filled triangles with apex pointing down), 400 ng (filled triangles with apex pointing up). In the case of negative controls (100 ng of unmethylated DNA without methylated DNA), a signal was not obtained (open squares).

FIG. 5 shows a rough diagram of the course of the methyl hairpin method. The Scorpion primer is found on the left side. The (methylation-specific) probe element of the Scorpion primer is present in the form of a hairpin. It bears a fluorescent dye (filled triangle) and a quencher (filled square), which are found in direct spatial proximity to one another due to the hairpin structure. The zigzag line characterizes the PCR stopper within the linker element. The DNA to be investigated, which is already bisulfited, is presented in the form of a double bar. One CG position within the DNA will be investigated. Only if the cytosine was originally methylated does the bisulfite treatment leave it unchanged. Unmethylated cytosines are converted into uracil (or thymine). After a thermal denaturation, the (here non-methylation-specific) primer element of the Scorpion primer can bind to the single-stranded DNA. A primer extension occurs by means of a polymerase. After another thermal denaturation the probe binds intramolecularly to the extended primer, as long as the extension product contains a CG dinucleotide. This is the case, however, only if the DNA to be investigated was originally methylated. Unmethylated cytosines lead to TG dinucleotides at which a probe binding does not occur (not shown). Due to the binding of the probe to the extended primer sequence, the hairpin is opened up and a fluorescent signal can be detected (modified figure according to Thelwell et al. 2000, loc. cit., p. 3753).

FIG. 6 shows a rough diagram of the course of the methyl duplex method. The Scorpion primer is found on the left side. The (methylation-specific) probe element of the Scorpion primer is present together with another oligonucleotide in the form of a double strand. The probe element bears a fluorescent dye (filled triangle). A quencher is bound to the other oligonucleotide (filled square). Both components are found in direct spatial proximity to one another due to the duplex. The zigzag line characterizes the PCR stopper within the linker element of the Scorpion primer. The DNA to be investigated, which is already bisulfited, is presented in the form of a double bar. One CG position within the DNA will be investigated. Only if the cytosine was originally methylated does the bisulfite treatment leave it unchanged. Unmethylated cytosines are converted into uracil (or thymine). After a thermal denaturation, the (here non-methylation-specific) primer element of the Scorpion primer can bind to the single-stranded DNA. A primer extension occurs by means of a polymerase. After another thermal denaturation, the duplex is separated from the probe and the other oligonucleotide binds intramolecularly to the extended primer, as long as the extension product contains a CG dinucleotide. This is the case, however, only if the DNA to be investigated was originally methylated. Unmethylated cytosines lead to TG dinucleotides to which the probe does not bind (not shown). Due to the binding of the probe to the extended primer sequence, the dye and quencher are separated and a fluorescent signal can be detected (modified figure according to Solinas et al. 2001, loc. cit., p. e96).

The invention claimed is:

1. A method for the detection of cytosine methylations in DNA obtained from tissue samples or bodily fluids, the method comprising the steps of:
   a) treating the DNA to be investigated with bisulfite;
   b) amplifying the treated DNA of step a) using a polymerase and a primer pair consisting of a forward primer and a reverse primer wherein the forward primer and reverse primer produce a primer extension product from each complementary strand of the treated DNA, wherein each of the primer extension products have sequences that are complementary to each other, wherein each of the forward primer and the reverse primer has a 5'-end joined with a probe via a linker, wherein at least one of the probes includes at least one methylation-specific CG dinucleotide, and wherein the secondary structure of each of the probes comprises a hairpin shape or a duplex structure, and wherein each of the probes comprises two signal components which are found in spatial proximity to one another in the inactive form, and which are separated from one another by the hybridization of the probe to the primer extension product;
   c) separating each of the primer extension products from its respective strand of treated DNA of step a);
   d) hybridizing each of the probes of step b) intramolecularly to their respective primer extension products, whereby the hybridization of at least one of the probes occurs only if the cytosine positions to be analyzed were initially methylated; and
   e) detecting whether a hybridization of the probes has occurred, whereby DNA from tissue samples or bodily fluids is analyzed.

2. The method according to claim 1, wherein amplifying the treated DNA is carried out using a polymerase chain reaction.

3. The method according to claim 2, wherein the polymerase chain reaction is carried out using methylation-sensitive PCR (MSP) or a methylation-specific blocker.

4. The method according to claim 1, wherein the two signal components comprise a quencher-fluorescent dye pair.

5. The method according to claim 1, wherein spatial separation of the two signal components in the inactive form is maintained by the secondary structure of the probes.

6. The method according to claim 1, wherein amplifying the treated DNA comprises amplifying several sequences simultaneously.

7. The method according to claim 1, wherein the probes of the forward primer and the reverse primer comprise different signal components such that each probe produces different signals.

8. The method according to claim 1, wherein one of the forward primer and the reverse primer comprises a methylation-specific probe and the other of the forward primer and the reverse primer comprises a non-methylation-specific probe.

9. The method according to claim 1, wherein one of the forward primer and the reverse primer comprises a methylation-specific probe and the other of the forward primer and the reverse primer comprises a mutation-specific or allele-specific probe.

10. The method according to claim 1, wherein amplifying the treated DNA comprises performing a non-methylation-specific PCR amplification, and wherein each of the signal components comprise a quencher and a dye molecule.

11. The method according to claim 1, wherein amplifying the treated DNA comprises methylation-sensitive PCR (MSP), wherein each of the signal components comprise a quencher and a dye molecule.

12. The method according to claim 1, wherein the amplification step comprises using a methylation-specific blocker, wherein each of the signal components comprise a quencher and a dye molecule.

13. The method according to claim 1, wherein the amplification step comprises a non-methylation-specific amplification, wherein each of the signal components comprise a dye molecule and another oligonucleotide comprises a quencher.

14. The method according to claim 1, wherein the signal components of each of the forward and reverse primers generate the same signals in the active form and wherein the probes hybridize to different, co-methylated positions of the treated DNA.

15. The method according to claim 1, wherein the signal components of each of the forward and reverse primers generate different signals and wherein the probes hybridize to different, co-methylated positions of the treated DNA.

16. The method according to claim 1, wherein the forward and reverse primers are not methylation-specific, wherein the signal components of each of the forward and reverse primers generate different signals and wherein the probe of one of the forward primer and the reverse primer hybridizes to methylation-specific positions in the DNA while the probe of the other of the forward primer and the reverse primer hybridizes to non-methylation-specific positions in the treated DNA.

* * * * *

```
                        SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: chemically treated genomic DNA (Homo sapiens)

<400> SEQUENCE: 1
gaagttgata gatgggtatt ttttga                                        26

<210> SEQ ID NO 2
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 2
cccccttcct aatcctcaa                                                19

<210> SEQ ID NO 3
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 3
gcggaatttg agaggcgta                                                19

<210> SEQ ID NO 4
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 4
gcgttgtgaa ttttggggag                                               20

<210> SEQ ID NO 5
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5
taatcctcaa cacttccctc acaacct                                       27

<210> SEQ ID NO 6
<211> LENGTH: 29
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6
ggcagcctag gtcgcgaggg aaggctgcc                                     29
```

<210> SEQ ID NO 7
<211> LENGTH: 128
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7
gaagttgata gatgggtatt ttttgacggg gggtaggggc ggaatttgag aggcgtaagg     60
cgttgtgaat tttggggagg ggggtagttt gtaggtcgcg agggaagcgt tgaggattag    120
gaaggggg                                                             128

<210> SEQ ID NO 8
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8 ccccttcct aatcctcaa                                                   19

<210> SEQ ID NO 9
<211> LENGTH: 74
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9
cgggattatt tttataaggt tcggaggtcg cgaggttttc gttggagttt cgtcgtcgta     60
gttttcgtta ttag                                                       74

<210> SEQ ID NO 10
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
gggattattt ttataaggtt                                                 20

<210> SEQ ID NO 11
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
tactcactaa taacaaaact ac                                              22

<210> SEQ ID NO 12
<211> LENGTH: 29
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12
ggcagccgtt ggagtttcgt cgggctgcc                                       29

```
<210> SEQ ID NO 13
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
tactcactaa taacaaaact ac                                              22

<210> SEQ ID NO 14
<211> LENGTH: 34
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14
ctaataacaa aaactacaac aacaaaactc caac                                 34

<210> SEQ ID NO 15
<211> LENGTH: 15
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15
gttggagttt cgtcg                                                      15

<210> SEQ ID NO 16
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
tactcactaa taacaaaact ac                                              22
```